United States Patent
Lee et al.

(10) Patent No.: US 11,331,256 B2
(45) Date of Patent: May 17, 2022

(54) COSMETIC COMPOSITION FOR BLOCKING FINE DUST

(71) Applicant: LG HOUSEHOLD & HEALTH CARE LTD., Seoul (KR)

(72) Inventors: Seong-Cheon Lee, Daejeon (KR); Hyeong-Jin Cho, Daejeon (KR); Ki-Young Kim, Daejeon (KR); Eui-Taek Jeong, Daejeon (KR); Yu-Mi Kim, Daejeon (KR); Nae-Gyu Kang, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 16/757,124

(22) PCT Filed: Oct. 18, 2017

(86) PCT No.: PCT/KR2017/011546
§ 371 (c)(1),
(2) Date: Apr. 17, 2020

(87) PCT Pub. No.: WO2019/078380
PCT Pub. Date: Apr. 25, 2019

(65) Prior Publication Data
US 2020/0246241 A1 Aug. 6, 2020

(51) Int. Cl.
*A61K 8/49* (2006.01)
*A61Q 19/00* (2006.01)

(52) U.S. Cl.
CPC ............ *A61K 8/4966* (2013.01); *A61K 8/496* (2013.01); *A61K 8/4946* (2013.01); *A61Q 19/00* (2013.01); *A61K 2800/10* (2013.01); *A61K 2800/30* (2013.01)

(58) Field of Classification Search
CPC .... A61K 8/4966; A61K 8/4946; A61K 8/496; A61K 2800/10; A61K 2800/30; A61K 8/49; A61Q 19/00
See application file for complete search history.

(56) References Cited

U.S. PATENT DOCUMENTS

| 6,193,960 B1 * | 2/2001 | Metzger ............... A61K 8/4966 424/400 |
| 2003/0069191 A1 | 4/2003 | Potin et al. |
| 2004/0047823 A1 * | 3/2004 | Catroux ............... A61K 8/4946 424/70.11 |
| 2014/0127275 A1 * | 5/2014 | Cohen .................... A01N 43/16 424/401 |

FOREIGN PATENT DOCUMENTS

| CN | 106727131 A | 5/2017 | |
| EP | 2682119 A1 * | 1/2014 | ......... A61K 31/4045 |
| EP | 3097905 A1 | 11/2016 | |
| KR | 10-1653755 B1 | 9/2016 | |
| KR | 10-1659456 B1 | 9/2016 | |
| KR | 10-2017-0106579 A | 9/2017 | |
| KR | 10-2017-0128138 A | 11/2017 | |
| WO | WO 2014/136993 A2 | 9/2014 | |

OTHER PUBLICATIONS

International Search Report issued in PCT/KR2017/011546 (PCT/ISA/210), dated Jul. 17, 2018.
Naver blog (damsluv), "Biotherm UV Supreme Suncreen", URL: http://blog.naver.com/damsluv/140207574742, Feb. 27, 2014, pp. 1-25 (Total No. pp. 28).
Naver blog (Happy Eunjin, sol_2love), "Laneige All Day Anti-Pollution Defender All Ingredients Analysis XD Ampoule + Essence Ingredient / Cosmetic Ingredient", http://blog.naver.com/sol_2love/220630554259, Feb. 18, 2016, pp. 1-7 (Total No. pp. 13).
"Lancome (Blanc Expert) Hanjimin essence lotion & upgraded UV Expert," Naver Blog, URL:http://cafe.naver.com/cosmania/11275733, Mar. 9, 2015, 10 pages, with English translation.
"Yuriage Aqua Fresh Sun Lotion (wiht Course Inside) Review," Naver Blog, URL:http://blog.naver.com/sununy78/140158113923, Apr. 29, 2012, 9 pages, with English machine translation.

* cited by examiner

*Primary Examiner* — Snigdha Maewall
(74) *Attorney, Agent, or Firm* — Birch, Stewart, Kolasch & Birch, LLP

(57) ABSTRACT

The present disclosure relates to a cosmetic composition for blocking fine dust. The composition according to the present disclosure can fundamentally prevent problems due to fine dust by reducing the attachment rate of fine dust attached to skin.

13 Claims, No Drawings

COSMETIC COMPOSITION FOR BLOCKING FINE DUST

TECHNICAL FIELD

The present disclosure relates to a cosmetic composition for blocking fine dusts.

BACKGROUND ART

In modern societies, fine dusts including automobile emissions, yellow dust flying through industrial zones in eastern China, or external contaminants may cause skin aging and skin problems in urban areas and industrial complexes.

Since the size of the fine dust is mostly 10 μm or less, it is much smaller than general dust (average size of 50 μm or more) (US Environmental Protection Agency (EPA)). According to the research of National Institute of Environmental Research (2006), it has been investigated that major components of the fine dusts in the metropolitan area are sulfates, nitrates, and secondary products from China. Fine dusts penetrate deep into the alveoli of humans and accumulates in the bronchus and lungs, which is a direct cause of various respiratory diseases, and it may decrease the body's immune function, and cause asthma and respiratory difficulty, and increase the concentration of heavy metals in the rain or snow due to long-distance travel. In skin, as the size of the fine dust is small, it can penetrate deep into pores easily. If the penetrated fine dusts are not removed cleanly, it may cause inflammation and trouble in skin, and therefore, it is important to block the fine dusts so that it cannot penetrate the skin.

As conventional technologies for blocking fine dusts, technologies of blocking fine dusts with the negative charge in the formulation using a repulsive force of the same charge, or preventing fine dusts from penetrating pores by forming a network on the skin surface are disclosed. However, there are problems in that in fact, the fine dusts can be not only negatively charge but also positively charge, and the effect of blocking fine dusts by the repulsive force of a specific charge is very insignificant, and a film-forming polymer cannot fundamentally prevent the fine dusts from attaching to the skin surface.

The fine dusts can be removed to some extent by cleansing, but the finer the stronger the adsorption power, so it is impossible to remove the fine dusts deeply penetrated into pores with normal cleansing, and therefore, there is a need for a technology for fundamentally blocking the fine dusts from attaching to skin.

DISCLOSURE

Technical Problem

A problem to be solved by the present disclosure is to provide a composition for blocking fine dusts which prevent problems due to fine dusts by reducing the amount of fine dusts attached to skin.

Technical Solution

To solve the problem, the present disclosure provides a composition, preferably, cosmetic composition, for blocking fine dusts comprising a compound containing an N-heterocycle as an active ingredient.

Conventionally, as a solution for fine dusts, a method for removing fine dusts attached to skin by cleansing, a method for blocking fine dusts using a negative charge repulsive force, a method for forming a network on the skin surface, and the like were used. However, the method for cleansing fine dusts attached to skin may cause a problem to skin as the fine dusts are already attached to skin, and be difficult to cleanse when they are already adsorbed to skin, as very fine dusts have strong absorption. In addition, the method for blocking fine dusts using a negative charge repulsive force has a problem in that the actual effect of blocking fine dusts is insignificant, as the fine dusts show not only negative charge but also positive charge, and the method for forming a network on the skin surface has a problem in that it is impossible to fundamentally prevent fine dusts from attaching on the skin surface. Accordingly, the present inventors have researched a component which is comprised in a cosmetic composition and blocks skin attachment of fine dusts themselves, and have experimentally confirmed that when a compound containing an N-heterocycle is comprised, the skin attachment of fine dusts can be significantly reduced, thereby completing the present disclosure.

The term used herein, "fine dust" means dust in a fine size of 10 μm or less. The dust is not limited to a specific component, and includes all the materials commonly called dust.

The term used herein, "blocking fine dust" means prevent the fine dusts from attaching to skin, and extensively, is a meaning including eliminating fine dusts attached to skin.

The present inventors have experimentally confirmed that the composition comprising a compound containing an N-heterocycle as an active ingredient prevents fine dusts from attaching to skin.

The term used herein, "compound comprising an N-heterocycle" means a compound containing a heterocycle comprising a nitrogen atom as a heteroatom.

Preferably, the N-heterocycle may be a saturated or unsaturated 5, 6 or 9-membered N-heterocycle. The examples of the 5-membered N-heterocycle include pyrrolidine, pyrroline, pyrrole, pyrazolidine, imidazolidine, pyrazoline, imidazoline, pyrazole, imidazole, triazole, tetrazole, oxazole, thiazole, oxadiazole, thiadiazole, and the like, but not limited thereto, and accordingly, the 5-membered N-heterocycle may be one or more selected from the group consisting of pyrrolidine, pyrroline, pyrrole, pyrazolidine, imidazolidine, pyrazoline, imidazoline, pyrazole, imidazole, triazole, tetrazole, oxazole, thiazole, oxadiazole, and thiadiazole. The examples of the 6-membered N-heterocycle include piperidine, piperazine, pyridine, pyridazine, pyrimidine, pyrazine, triazine, oxazine, thiomorpholine, thiazine, cytosine, thymine, uracil, thiomorpholine dioxide, and the like, but not limited thereto, and accordingly, the 6-membered N-heterocycle may be one or more selected from the group consisting of piperidine, piperazine, pyridine, pyridazine, pyrimidine, pyrazine, triazine, oxazine, thiomorpholine, thiazine, cytosine, thymine, uracil and thiomorpholine dioxide.

In addition, in one preferable example of the present disclosure, the present inventors have experimentally confirmed that the composition comprising a compound containing a 9-membered N-heterocycle in which a 5-membered N-heterocycle binds with a benzene ring as an active ingredient prevents fine dusts from attaching to skin.

The examples of the 9-membered N-heterocycle include indoline, indole, isoindole, indazole, benzimidazole, azaindole, and the like, but not limited thereto, and accordingly, the 9-membered N-heterocycle may be one or more selected from the group consisting of indoline, indole, isoindole, indazole, benzimidazole and azaindole.

More preferably, to achieve the object of the present disclosure, the N-heterocycle may be a 6-membered N-heterocycle or 9-membered N-heterocycle, and much more preferably, may be one or more selected from the group consisting of triazine, benzotriazole and benzimidazole.

Most preferably, the compound comprising an N-heterocycle may be bis-ethylhexyloxyphenol methoxyphenyl triazine, melamine (1,3,5-triazine-2,4,6-triamine), methylene bis-benzotriazolyl tetramethylbutylphenol, ethylhexyl triazone, phenyl benzimidazole sulfonic acid, diethylhexyl butamido triazone, disodium phenyl dibenzimidazole tetrasulfonate, drometrizole trisiloxane, trisbiphenyl triazine. The present inventors have prepared a cosmetic composition comprising the above materials, and have experimentally confirmed that it can significantly reduce attachment of fine dusts to skin.

The compound comprising an N-heterocycle can block fine dusts by neutralizing a fine charge present on a surface of skin or an object, and is not limited to this theory.

In addition, the compound comprising an N-heterocycle has an effect of preventing or blocking attachment of heavy metals.

Preferably, the molecular weight of the compound comprising an N-heterocycle may be 100 to 1,000, more preferably 200 to 800, much more preferably 300 to 700.

Herein, the compound comprising an N-heterocycle may be comprised in an amount of 0.1 to 10% by weight, based on the total weight of the composition, and it may be comprised in an amount of preferably, 0.5 to 8% by weight, more preferably, 1 to 5% by weight. When it is comprised over 10% by weight, the feeling of the formulation may be sticky, oily, and greasy, and the stability of the formulation may be reduced.

Furthermore, the cosmetic composition for blocking fine dusts according to the present disclosure may be prepared by suitably mixing components mixed to common cosmetics such as a moisturizer, a thickener, powder, alcohol, a natural polymer, a synthetic polymer, a saccharide, an antioxidant, buffer, various kinds of extracts, a stabilizer, a preservative, a coloring, or a flavoring, in addition to the active ingredient, according to common methods. The moisturizer may be glycerin, sorbitol, butylene glycol, dipropylene glycol, propylene glycol, pentylene glycol, propanediol, 1,2-hexanediol, octanediol, or natural product-derived extract, or the like.

It comprises other residual amounts of water.

In addition, the cosmetic composition for blocking fine dusts according to the present disclosure may be prepared in a formulation selected from the group consisting of solution, ointment for external application, cream, foam, nutritional cosmetic water, soft cosmetic water, soft water, milky lotion, makeup base, essence, liquid cleanser, bath preparation, sun screen cream, sun oil, suspension, emulsion, paste, gel, lotion, powder, oil, powder foundation, emulsion foundation, wax foundation, patch, mist and spray, and the like, but not limited thereto.

In one embodiment of the present disclosure, the compound comprising an N-heterocycle may be comprised in an oil-dispersed form. This means a form in which oils are added for dissolution of the corresponding compound according to common characteristics of the compound comprising an N-heterocycle.

In this case, the cosmetic composition of the present disclosure may have an oil formulation, and for dissolution of the compound comprising an N-heterocycle, it may further comprise a polar oil and/or silicon oil, and for example, it includes dicaprylyl carbonate, caprlic/capric triglyceride, isopropyl palmitate, C12-15 alkyl benzoate, propyl heptyl caprylate, coco-caprylate/caprate, dibutyl adipate, triethyl hexanoin, phenyl trimethicone, cyclopentasiloxane, cyclohexasiloxane, caprylyl trimethicone, and the like, but not limited thereto. In other words, the cosmetic composition according to the present disclosure may be prepared by dissolving the compound comprising an N-heterocycle in an oil (or oil phase).

In other embodiment of the present disclosure, the compound comprising an N-heterocycle may be comprised in a water-dispersed form.

Commonly, the compound comprising an N-heterocycle is oil-soluble and therefore it should be dispersed by adding oils, but the present disclosure allows the compound comprising an N-heterocycle to be dispersed in water without adding oils, and provides a cosmetic composition which comprises an N-heterocycle and is also a hydration formulation.

The hydration formulation may be a formulation selected from the group consisting of water gel, solution, foam, cosmetic water, milky lotion, suspension, emulsion, paste, lotion, patch, mist and spray formulations, but not limited thereto.

As above, the compound comprising an N-heterocycle may be in a form with enhanced solubility or dispersibility for water as mixed and treated with other compounds. When the dispersibility for water is excellent, it may be usefully used for a cosmetic composition comprising a large amount of water, and it is possible to minimize or eliminate the amount of oils in the composition.

As a water-dispersed form of the compound comprising an N-heterocycle, it is also possible to purchase and use a commercially available raw material, and for example, it is possible to purchase and use a raw material of BASF corporation (brand name: Tinosorb® S Aqua).

Advantageous Effects

The composition according to the present disclosure can fundamentally prevent problems due to fine dusts by lowering the attachment rate of fine dusts attached to skin.

DETAILED DESCRIPTION OF THE EMBODIMENTS

Hereinafter, the present disclosure will be described in detail by examples to specifically described the present disclosure. However, the examples according to the present disclosure may be modified into various other forms, and the scope of the present disclosure should not be construed to be limited by the examples described below. The examples of the present disclosure are provided to illustrate the present disclosure more completely.

Experimental Example 1: Preparation of Example 1 and Comparative Examples 1-3 and Estimation of Fine Dust Attachment The present inventors prepared essences having the composition of the following Table 1 by a common method, for an experiment of estimation of fine dust attachment.

TABLE 1

| Raw material | Example 1 Content(% by weight) | Comparative example 1 Content(% by weight) | Comparative example 2 Content(% by weight) | Comparative example 3 Content(% by weight) |
|---|---|---|---|---|
| Purified water | To 100 | To 100 | To 100 | To 100 |
| Glycerin | 3 | 3 | 3 | 3 |
| Butylene glycol | 6 | 6 | 6 | 6 |
| 1,2-hexanediol | 1.5 | 1.5 | 1.5 | 1.5 |
| Stearic acid | 0.3 | 0.3 | 0.3 | 0.3 |
| Cetearyl glucoside | 0.2 | 0.2 | 0.2 | 0.2 |
| Cetearyl alcohol | 0.8 | 0.8 | 0.8 | 0.8 |
| Methyl glucose sesquistearate | 1 | 1 | 1 | 1 |
| Glyceryl stearate | 0.5 | 0.5 | 0.5 | 0.5 |
| Phenyl trimethicone | 4 | 4 | 4 | 4 |
| Cyclopentasiloxane | 4 | 4 | 4 | 4 |
| Cyclohexasiloxane | 2 | 2 | 2 | 2 |
| Bis-ethylhexyl-oxyphenol methoxyphenyl triazine[1] | 2.0 | — | — | — |
| Arachidyl glucoside | — | 2.0 | — | — |
| Isostearyl isostearate | — | — | 2.0 | — |
| Flavoring | 0.1 | 0.1 | 0.1 | 0.1 |

[1]Tinosorb® S, BASF

1) Method for Estimating Fine Dust Attachment i) After applying artificial sebum of 1.3 mg/cm² on a PMMA plate, it was dried for 15 minutes.

ii) After applying a test formulation on the dried artificial sebum in the same amount, it was dried for 15 minutes (Noting was applied on the control group).

iii) The PMMA plate was attached on the internal top of the self-made chamber, and a pan on the bottom of the chamber was operated for 5 minutes, to expose 0.5 g substitutive fine dusts (brand name LM-YG0510, comprising strontium carbonate, alumina, europium oxide, and dysprosium oxide).

iv) Using a magnifying glass (Aphrodite-3, 50×), UV images were photographed (measuring 4 points per plate).

v) Using ImagePro Plus, the area of dust attachment was measured.

vi) The fine dust attachment rate was calculated by comparing the sample with the result of 3 times of experiments (Setting the fine dust attachment rate of the control group to 100).

2) Result

As a result, as shown in Table 2, it was confirmed that Example 1 showed the relative attachment rate of less than ⅓ compared to the control group, and it has an excellent effect of prevent fine dust attachment as much as showing the relative attachment rate of less than ½ compared to the Comparative examples 1-3.

TABLE 2

| | Example 1 | Comparative example 1 | Comparative example 2 | Comparative example 3 | Control group |
|---|---|---|---|---|---|
| Fine dust attachment rate (%) | 28.97 | 88.31 | 89.85 | 63.90 | 100 |

Experimental Example 2: Preparation of Example 2 and Comparative Examples 4-8 and Estimation of Fine Dust Attachment The present inventors prepared essences having the composition of the following Table 3 by a common method, for an experiment of estimation of fine dust attachment.

TABLE 3

| Raw material | Example 2 Content(% by weight) | Comparative example 4 Content(% by weight) | Comparative example 5 Content(% by weight) | Comparative example 6 Content(% by weight) | Comparative example 7 Content(% by weight) | Comparative example 8 Content(% by weight) |
|---|---|---|---|---|---|---|
| Purified water | To 100 | To 100 | To 100 | To 100 | To 100 | To 100 |
| Glycerin | 3 | 3 | 3 | 3 | 3 | 3 |
| Butylene glycol | 6 | 6 | 6 | 6 | 6 | 6 |
| 1,2-hexanediol | 1.5 | 1.5 | 1.5 | 1.5 | 1.5 | 1.5 |
| Stearic acid | 0.3 | 0.3 | 0.3 | 0.3 | 0.3 | 0.3 |
| Cetearyl glucoside | 0.2 | 0.2 | 0.2 | 0.2 | 0.2 | 0.2 |
| Cetearyl alcohol | 0.8 | 0.8 | 0.8 | 0.8 | 0.8 | 0.8 |
| Bis-ethylhexyloxyphenol methoxyphenyl triazine water dispersion[2] | 0.5 | — | — | — | — | — |
| Amodimethicone | — | 0.5 | — | — | — | — |
| Polyquaternium-10 | — | — | 0.5 | — | — | — |
| Polymethylmethacrylate | — | — | — | 0.5 | — | — |
| Aminomethylpropanol | — | — | — | — | 0.5 | — |
| Flavoring | 0.1 | 0.1 | 0.1 | 0.1 | 0.1 | 0.1 |

[2]Tinosorb® S Aqua, BASF

As a result, as shown in Table 4, it was confirmed that Example 2 showed the relative attachment rate of about ¼ compared to the control group, and it has an excellent effect of prevent fine dust attachment as much as showing the relative attachment rate of less than ⅓ compared to the Comparative examples 4-8.

In addition, as the result of confirming the effect of preventing fine dust attachment of other compounds comprised in the bis-ethylhexyloxyphenol methoxyphenyl triazine water dispersion (Tinosorb® S Aqua, BASF) of Example 2 through Comparative examples 6 and 7, it was confirmed that other compounds other than bis-ethylhexyloxyphenol methoxyphenyl triazine had no effect of preventing fine dust attachment.

TABLE 4

|  | Example 2 | Comparative example 4 | Comparative example 5 | Comparative example 6 | Comparative example 7 | Comparative example 8 | Control group |
|---|---|---|---|---|---|---|---|
| Fine dust attachment rate (%) | 25.21 | 89.66 | 91.10 | 92.52 | 80.77 | 77.68 | 100 |

Experimental Example 3: Preparation of Example 3 and Comparative Example 9 and Estimation of Fine Dust Attachment The present inventors prepared water-gel formulations of Example 3 and Comparative example 9 by the content shown in the following Table 5, and progressed the estimation of fine dust attachment.

TABLE 5

| Raw material INCI name | Example 3 Content(% by weight) | Comparative example 9 Content(% by weight) |
|---|---|---|
| Purified water | To 100 | To 100 |
| Glycerin | 4 | 4 |
| PEG-5 | 2 | 2 |
| 1,2-hexanediol | 1 | 1 |
| Ammonium acryloyldimethyltaurate/VP copolymer | 0.4 | 0.4 |
| melamine | 0.5 | — |

As a result, as shown in Table 6, it was confirmed that Comparative example 9 had no effect of preventing fine dust attachment compared to the control group in which nothing was applied, and rather fine dust attached better, while Example 3 showed the relative attachment rate of less than 85% compared to the control group and that of less than ½ compared to the Comparative example 9, and thereby an excellent effect of preventing fine dust attachment of melamine (1,3,5-triazine-2,4,6-triamine) characteristically contained in Example 3 was confirmed.

TABLE 6

|  | Example 3 | Comparative example 9 | Control group |
|---|---|---|---|
| Fine dust attachment rate (%) | 82.1 | 178.5 | 100 |

Experimental Example 4: Preparation of Examples 4-6 and Comparative Examples 10-12 and Estimation of Fine Dust Attachment The present inventors prepared emulsion formulations of Examples 4-6 and Comparative examples 10-12 by the content shown in the following Table 7, and progressed the estimation of fine dust attachment.

TABLE 7

| Raw material INCI name | Example 4 Content (% by weight) | Example 5 Content (% by weight) | Example 6 Content (% by weight) | Comparative example 10 Content(% by weight) | Comparative example 11 Content(% by weight) | Comparative example 12 Content(% by weight) |
|---|---|---|---|---|---|---|
| Hydrogenated polydecene | 3 | 3 | 3 | 3 | 3 | 3 |
| Cyclopentasiloxane | 5 | 5 | 5 | 5 | 5 | 5 |
| Cetearyl alcohol | 1.5 | 1.5 | 1.5 | 1.5 | 1.5 | 1.5 |
| Ceteareth-6 Olivate | 1.2 | 1.2 | 1.2 | 1.2 | 1.2 | 1.2 |
| Shea butter | 3 | 3 | 3 | 3 | 3 | 3 |
| Isostearate | 1 | 1 | 1 | 1 | 1 | 1 |
| Phenethylbenzoate | 2 | 2 | 2 | 2 | 2 | 2 |
| Purified water | To 100 | To 100 | To 100 | To 100 | To 100 | To 100 |
| Xanthan gum | 0.2 | 0.2 | 0.2 | 0.2 | 0.2 | 0.2 |
| Acrylate/C10-30 alkyl acrylate crosspolymer | 0.02 | 0.02 | 0.02 | 0.02 | 0.02 | 0.02 |
| Hydrogenated lecithin | 0.5 | 0.5 | 0.5 | 0.5 | 0.5 | 0.5 |
| Trisodium EDTA | 0.02 | 0.02 | 0.02 | 0.02 | 0.02 | 0.02 |
| Pantenol | 1 | 1 | 1 | 1 | 1 | 1 |
| Glycerin | 5 | 5 | 5 | 5 | 5 | 5 |
| Butylene glycol | 3 | 3 | 3 | 3 | 3 | 3 |
| 1,2-hexanediol | 1 | 1 | 1 | 1 | 1 | 1 |
| Tromethamine | 0.02 | 0.02 | 0.02 | 0.02 | 0.02 | 0.02 |
| Flavoring | 0.12 | 0.12 | 0.12 | 0.12 | 0.12 | 0.12 |
| Methylene Bis-Benzotriazolyl tetramethyl butylphenol | 4 | — | — | — | — | — |
| Ethylhexyl triazone | — | 2 | — | — | — | — |

TABLE 7-continued

| Raw material INCI name | Example 4 Content (% by weight) | Example 5 Content (% by weight) | Example 6 Content (% by weight) | Comparative example 10 Content(% by weight) | Comparative example 11 Content(% by weight) | Comparative example 12 Content(% by weight) |
|---|---|---|---|---|---|---|
| Phenylbenzimidazole sulfonic acid | — | — | 2 | — | — | — |
| Ethylhexylmethoxy Cinnamate | — | — | — | — | 6 | — |
| Ethyl hexyl Salicylate | — | — | — | — | — | 4.5 |

As a result, as shown in Table 8, it was confirmed that even Comparative examples 10-12 had a slight effect of preventing fine dust attachment compared to the control group in which nothing was applied, but Example 4, Example 5 and Example 6 showed the relative attachment rate of less than ⅓ compared to the control group, about ⅓ of the control group, and less than ½ compared to the control group, respectively, and thereby, an excellent effect of preventing fine dust attachment of Methylene Bis-Benzotriazolyl tetramethyl butylphenol, ethylhexyl triazone, and phenylbenzimidazole sulfonic acid characteristically contained in Examples 4, 5 and 6, respectively.

TABLE 8

| | Example 4 | Example 5 | Example 6 | Comparative example 10 | Comparative example 11 | Comparative example 12 | Control group |
|---|---|---|---|---|---|---|---|
| Fine dust attachment rate (%) | 31.43 | 34.45 | 45.21 | 87.23 | 79.63 | 85.21 | 100 |

Methylene Bis-Benzotriazolyl tetramethyl butylphenol having benzotriazole, ethylhexyl triazone having triazine, and phenylbenzimidazole sulfonic acid having benzimidazole, which are N-heterocyclic structures, showed an excellent effect of reducing fine dust attachment compared to other compounds.

Experimental Example 5: Preparation of Examples 7-10 and Comparative Examples 13-15 and Estimation of Fine Dust Attachment The present inventors prepared cream formulations of Examples 7-10 and Comparative examples 13-15 by the content shown in the following Table 9, and progressed the estimation of fine dust attachment.

TABLE 9

| Raw material INCI name | Example 7 Content (% by weight) | Example 8 Content (% by weight) | Example 9 Content (% by weight) | Example 10 Content (% by weight) | Comparative example 13 Content(% by weight) | Comparative example 14 Content(% by weight) | Comparative example 15 Content(% by weight) |
|---|---|---|---|---|---|---|---|
| Cetearyl alcohol | 2 | 2 | 2 | 2 | 2 | 2 | 2 |
| Beeswax | 2 | 2 | 2 | 2 | 2 | 2 | 2 |
| Glyceryl stearate | 1 | 1 | 1 | 1 | 1 | 1 | 1 |
| PEG-100 stearate | 1 | 1 | 1 | 1 | 1 | 1 | 1 |
| Sucrose polystearate | 2 | 2 | 2 | 2 | 2 | 2 | 2 |
| Triethylhexanoin | 2 | 2 | 2 | 2 | 2 | 2 | 2 |
| Dimethicone | 5 | 5 | 5 | 5 | 5 | 5 | 5 |
| Caprylyl trimethicone | 5 | 5 | 5 | 5 | 5 | 5 | 5 |
| Purified water | To 100 | To 100 | To 100 | To 100 | To 100 | To 100 | To 100 |
| Acrylate/C10-30 alkyl acrylate crosspolymer | 0.1 | 0.1 | 0.1 | 0.1 | 0.1 | 0.1 | 0.1 |
| Xanthan gum | 0.1 | 0.1 | 0.1 | 0.1 | 0.1 | 0.1 | 0.1 |
| Carbomer | 0.2 | 0.2 | 0.2 | 0.2 | 0.2 | 0.2 | 0.2 |
| Propandiol | 3 | 3 | 3 | 3 | 3 | 3 | 3 |
| Glycerin | 5 | 5 | 5 | 5 | 5 | 5 | 5 |
| Butylene glycol | 6 | 6 | 6 | 6 | 6 | 6 | 6 |
| 1,2-hexandiol | 1 | 1 | 1 | 1 | 1 | 1 | 1 |
| Tromethamine | 0.08 | 0.08 | 0.08 | 0.08 | 0.08 | 0.08 | 0.08 |
| Flavoring | 0.1 | 0.12 | 0.12 | 0.12 | 0.12 | 0.12 | 0.12 |
| Diethylhexyl butamido triazone | 3 | — | — | — | — | — | — |

TABLE 9-continued

| Raw material INCI name | Example 7 Content (% by weight) | Example 8 Content (% by weight) | Example 9 Content (% by weight) | Example 10 Content (% by weight) | Comparative example 13 Content (% by weight) | Comparative example 14 Content (% by weight) | Comparative example 15 Content (% by weight) |
|---|---|---|---|---|---|---|---|
| Disodium phenyl dibenzimidazole tetrasulfonate | — | 3 | — | — | — | — | — |
| Drometrizole trisiloxane | — | — | 3 | — | — | — | — |
| Trisbiphenyl triazine | — | — | — | 3 | — | — | — |
| Ethylhexylmethoxy cinnamate | — | — | — | — | — | 6 | — |
| Ethylhexyl salicylate | — | — | — | — | — | — | 4.5 |

As a result, as shown in Table 10, it was confirmed that even Comparative examples 13-15 had few effect of preventing fine dust attachment compared to the control group in which nothing was applied, but Examples 7-10 showed the relative attachment rate of less than ½ compared to the control group, respectively, and thereby, an excellent effect of preventing fine dust attachment of Diethylhexyl butamido triazone, disodium phenyl dibenzimidazole tetrasulfonate, and trisbiphenyl triazine characteristically contained in Examples 7-10, respectively.

TABLE 10

| | Example 7 | Example 8 | Example 9 | Example 10 | Comparative example 13 | Comparative example 14 | Comparative example 15 | Control group |
|---|---|---|---|---|---|---|---|---|
| Fine dust attachment rate (%) | 42.55 | 39.69 | 45.81 | 40.07 | 98.12 | 91.45 | 88.87 | 100 |

Diethylhexyl butamido triazone having triazine, disodium phenyl dibenzimidazole tetrasulfonate having benzimidazole, and trisbiphenyl triazine having benzotriazole, which are N-heterocyclic structures, showed an excellent effect of reducing fine dust attachment compared to other compounds.

The invention claimed is:

1. A method for lowering attachment of fine dusts to skin by applying an effective amount of a compound containing an N-heterocycle into skin of a person in need thereof,
    wherein the compound containing an N-heterocycle is one or more selected from the group consisting of bis-ethylhexyloxyphenol methoxyphenyl triazine, melamine (1,3,5-triazine-2,4,6-triamine), methylene bis-benzotriazolyl tetramethylbutylphenol, ethylhexyl triazone, phenyl benzimidazole sulfonic acid, diethylhexyl butamido triazone, disodium phenyl dibenzimidazole tetrasulfonate, drometrizole trisiloxane, and trisbiphenyl triazine,
    wherein an attachment rate of fine dusts attached to skin is reduced to 85% or less compared to a control group that does not use the effective amount of said N-heterocycle.

2. The method according to claim 1,
    wherein the compound containing an N-heterocycle is comprised in a cosmetic composition as a fine dust blocking agent, and the compound comprising an N-heterocycle is applied into skin by applying the cosmetic composition into skin.

3. The method according to claim 2,
    wherein the fine dust blocking agent consists of the compound containing an N-heterocycle.

4. The method according to claim 1,
    wherein the compound containing an N-heterocycle is comprised in a water-dispersed form.

5. The method according to claim 2,
    wherein the cosmetic composition does not comprise an oil component.

6. The method according to claim 2,
    wherein the cosmetic composition is a hydration formulation.

7. The method according to claim 6,
    wherein the hydration formulation is a formulation selected from the group consisting of water gel, solution, foam, cosmetic water, milky lotion, suspension, emulsion, paste, lotion, patch, mist and spray formulations.

8. The method according to claim 2,
wherein the compound containing an N-heterocycle is comprised in an amount of 0.1 to 10% by weight based on the total weight of the composition.

9. The method according to claim 1, wherein the attachment rate of fine dusts attached to skin is reduced to less than ½ compared to a control group that does not use the effective amount of said N-heterocycle.

10. The method according to claim 1, wherein the attachment rate of fine dusts attached to skin is reduced to less than ⅓ compared to a control group that does not use the effective amount of said N-heterocycle.

11. The method according to claim 1, wherein the attachment rate of fine dusts attached to skin is reduced to about ¼ compared to a control group that does not use the effective amount of said N-heterocycle.

12. The method according to claim 1, wherein the compound containing an N-heterocycle is comprised in an amount of 0.5 to 8% by weight based on the total weight of the composition.

13. The method according to claim 1, wherein the compound containing an N-heterocycle is comprised in an amount of 1 to 5% by weight based on the total weight of the composition.

* * * * *